United States Patent [19]
Mason

[11] Patent Number: 4,964,708
[45] Date of Patent: Oct. 23, 1990

[54] MICROSCOPE FOR MEDICAL SURGERY

[76] Inventor: Michael S. Mason, 10950 NW. Lost Park Dr., Portland, Oreg. 97229

[21] Appl. No.: 380,884

[22] Filed: Jul. 14, 1989

[51] Int. Cl.⁵ ............................................. G02B 21/20
[52] U.S. Cl. ..................................... 350/519; 350/502
[58] Field of Search ............... 350/519, 523, 524, 525, 350/526, 527, 528, 511, 512, 513, 514, 515, 507, 502, 522, 518, 286, 287, 517, 146, 147

[56] References Cited
U.S. PATENT DOCUMENTS

| | | | |
|---|---|---|---|
| 3,186,300 | 6/1965 | Littman | 350/515 |
| 3,353,892 | 11/1967 | Minns et al. | 350/516 |
| 3,741,622 | 6/1973 | Cox | 350/503 |
| 3,909,106 | 9/1975 | Buhler | 350/516 |
| 4,009,930 | 3/1977 | Abe et al. | 350/516 |
| 4,871,245 | 10/1985 | Ishikawa et al. | 350/502 |

*Primary Examiner*—Bruce Y. Arnold
*Assistant Examiner*—T. V. Tran

[57] ABSTRACT

A binocular microscope having a range of variable magnifications extending from 4X to 20X that is suited to microsurgery and other applications. The microscope has a folded optical axis that places the eyepiece directly in line with the work area. The projected line of sight of a viewer looking through the eyepiece is incident on the work area. This enables the viewer to have normal eye-hand coordination. The folded optical axis also provides a compact configuration that provides a large, clear and unobstructed access to the work area.

5 Claims, 2 Drawing Sheets

MICROSCOPE FOR MEDICAL SURGERY

BACKGROUND OF THE INVENTION

1. Field of the Invention

This invention relates to a binocular microscope having a range of variable magnifications and more particularly to a binocular microscope utilized in micro-surgery which accommodates the natural eye-hand coordination of the surgeon.

2. Background Information

Microscopes are used by surgeons for operating in situations where viewing fine detail is critical. Operating on a patient's brain is but one example of such a situation. In a typical operating setting, the patient is prone on the operating table and the microscope is positioned above the area being operated on. This "area" is hereafter sometimes referred to as the work area. Care is taken to see that the work area is accessible so as to enable the surgeon to see the work area and also to enable the surgeon to manipulate the surgical instruments within the work area.

Microscopes in use prior to this invention provided the desirable features of a binocular type eyepiece through which the surgeon views the area; zoom lens capabilities to allow the surgeon to increase or decrease the magnification of the area; a second binocular type eyepiece for viewing by an assistant; and a viewing lens for taking photographs or video recordings.

To provide an unobstructed view of the area being worked on, the microscope is placed above and directed vertically onto the work area. The lenses, including the zoom system, is encased in the vertically oriented housing of the microscope. The surgeon, however, cannot conveniently look straight down through the microscope due to its length which would position the surgeon too far from the work area. Thus, the eyepiece is placed at an angle to the housing of the microscope so that viewing the work area is possible with a more natural positioning of the head. This angular positioning is accomplished with mirrors and/or prisms and is well known to the art.

There are many different kinds of operating microscopes but, from what is known, they all have a common problem. The projected line of sight through the eyepiece is not directly aimed at the work area. This is due to the fact that the eyepiece is at an angle with respect to the housing of the microscope. The eyepiece, in other words, directs the surgeon's eyes away from, rather than coincident with the work area. This is unnatural in that the surgeon is looking in a direction toward one area while his hands are required to work in another.

BRIEF DESCRIPTION OF THE INVENTION

The present invention solves the problem of the surgeon not looking directly at the work area by constructing the microscope in a folded configuration having three basic sections; an objective section, a zoom section and an eyepiece section. The objective section is directed vertically upward from its in-line view of the work area, and the zoom section extends laterally and downwardly from the upper end of the objective section toward the operator, e.g. at an angle of about 30° from horizontal. The eyepiece extends upwardly from the opposite end of the zoom section, e.g. at about a 60° angle from horizontal and at right angle to the zoom section.

This general arrangement when coordinated with the required length of the components places the line of sight through the eyepiece such that it is aligned with and directed toward the work area. An image from the work area is directed vertically up through the objective section where it is folded or reflected by a mirror into and through the zoom section. The image is then folded upwardly by mirrors from the zoom section through the eyepiece section.

In general, a surgeon is most comfortable looking downward toward the work area at an angle of about 30° from the vertical (60° from horizontal) with the work area about 16–18 inches from the eyes. The eyepiece is desirably inclined so that its viewing axis is directed toward the work area. This is provided by establishing the above relationship between the three sections. Viewing the work area directly, in a straight line with the direction of the eyepiece, provides the best and most natural normal eye-hand coordination during surgery.

The main factor that needs to be considered is the projected line of sight through the eyepiece, i.e. that it is directed toward the work area and not away from it. This is accomplished by providing for the optical axis through the objective section to be coincident with the axis of the eyepiece, with the work area about 17 inches from the eye rest of the eyepiece. The folded arrangement of the three sections provides for a packaging of the components which permits the surgeon to look directly at the work area. It also provides a fairly large, clear and unobstructed space between the objective section of the microscope and the work area which is necessary for the manipulation of surgical instruments.

The invention will be more clearly understood and appreciated with reference to the following detail description and the drawings referred to therein.

DESCRIPTION OF THE PREFERRED EMBODIMENT

Figure 4:
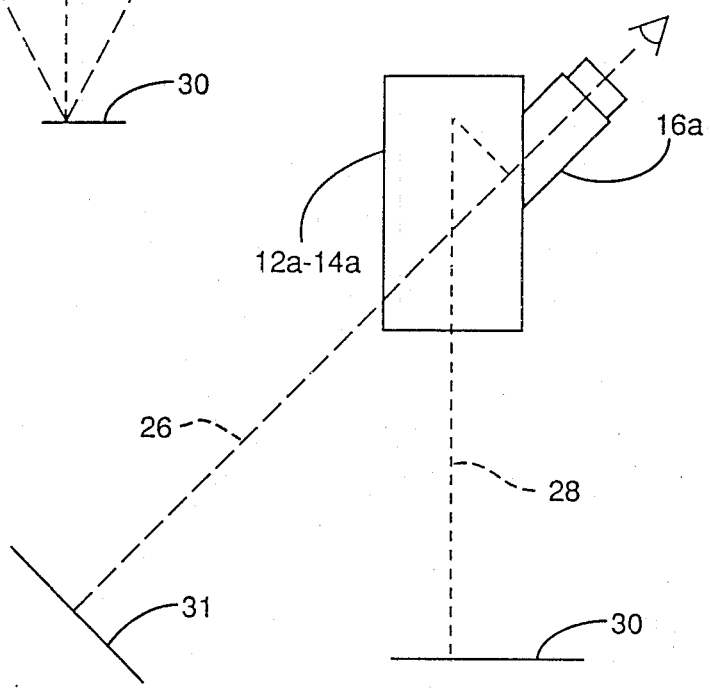
FIG. 4 is a microscope of the prior art.

FIG. 4 is a typical arrangement of a microscope of the prior art. There are variations to the arrangement but as far as known, they all lack the advantages of the present invention. As shown in FIG. 4, the projected line of sight 26 of a viewer looking through the eyepiece 16a is at an angle to the zoom/objective housing 12a–14a. It is not aimed directly at the work area 30. Instead the projected line of sight is aimed at an imaginary work area 31. This would be the area where a user's hands might naturally be placed when looking into the eyepiece. A user would therefore have to adjust the position of his/her hands or instruments from the imaginary work area 31 to the actual work area 30.

Figure 1:
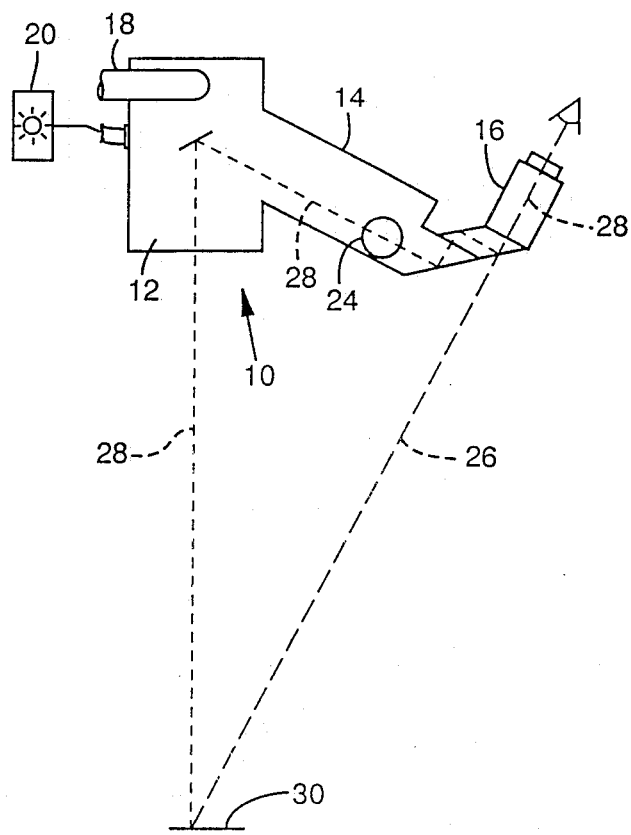
FIG. 1 is a diagrammatical view of the microscope.
Figure 2:
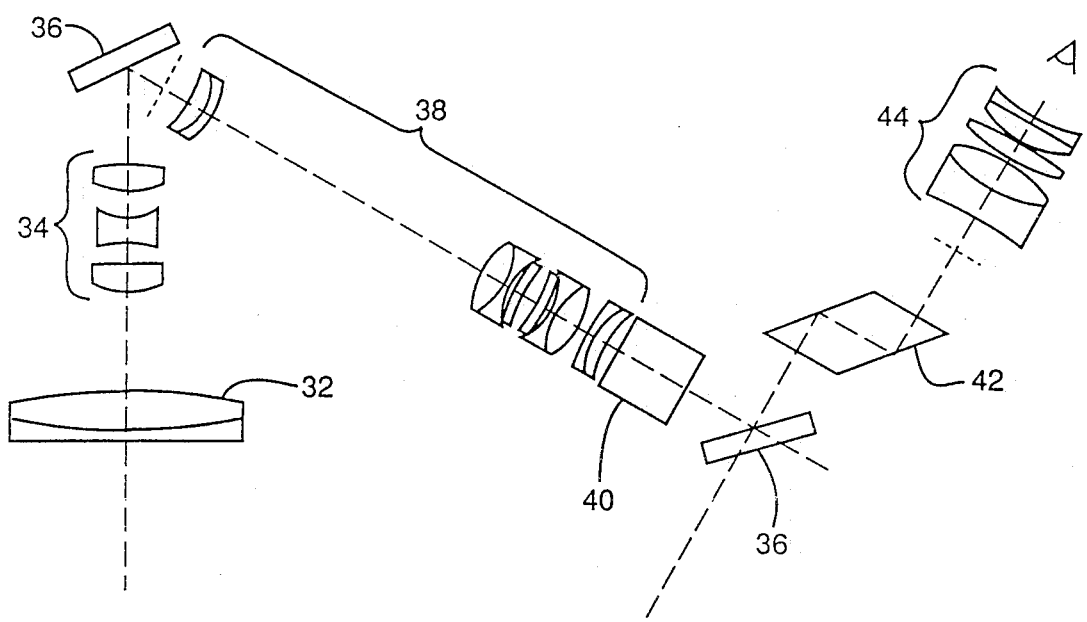
FIG. 2 illustrates the arrangement of the lens groups within the microscope of FIG. 1.

Referring to FIGS. 1 and 2, a binocular microscope 10 having a range of variable magnifications and dual viewing channels is shown positioned above and with the optics focused on the work area 30.

The microscope 10 can be categorized as having three main sections; an objective section 12, which is vertically positioned over the work area, a zoom section 14, that extends laterally from the objective section 12 to an eyepiece section 16 that is extended from the end of the zoom section as needed to project the line of sight 26, at the work area 30.

The microscope 10 has a mounting bracket 18 affixed to the objective section 12 for attachment to a supporting member (not shown). The supporting member, as typical for operating microscopes, has adjusting mechanisms to position and focus the microscope relative to the work area 30. The objective section 12 also has provision for illumination of the work area by a light source 20.

The zoom section 14 has a cammed mechanical arrangement that is typical for operating microscopes for changing the relative positions of the movable lens groups to vary the magnification over the full range. Auxiliary channels 24 are provided in the zoom section for either monocular viewing or adaptation to camera or video recording equipment.

The eyepiece section 16 is where the operator looks into the system and it is equipped with rhomboid prisms 42 arranged for inter-pupillary adjustment of the eyepieces.

FIG. 1 illustrates the arrangement of the three sections 12, 14 and 16 of the microscope 10 with the objective section 12 being vertically aligned relative to the work area 30. The zoom section 14 extends laterally from the objective section and is angled downwardly somewhat from horizontal. The eyepiece section 16 is mounted at the outer end of the zoom section with the eyepieces projecting upward from the zoom section an angle that enables the viewer to comfortably look through the eyepiece with the line of sight directed at the work area.

The optical elements of the microscope 10 are shown in FIG. 2. The objective section 12 has a collimating lens 32, an objective lens 34 and a mirror 36. The zoom section 14 has the moving group of lenses 38 that permit the viewer (or user) to vary the magnification, most often referred to as a zoom lens, a beam splitter 40 and a mirror 36. The eyepiece section has a rhomboid prism 42 and the eyepiece lenses 44.

A dash line 28 represents the optical axis and the dashed line 26 represents the projected line of sight as shown in FIGS. 1 and 2. The optical axis is the path that a central beam of an image traverses through the optical elements of the three sections 12, 14 and 16 of microscope 10. The projected line of sight 26 as indicated is a straight line through the eyepiece 16 of the microscope; it is the line of sight which a viewer perceives as being true.

As illustrated in the figures, the optical axis 28 and the projected line of sight 26 intersect at or in close proximity to the work area 30.

The arrangement of the three sections 12, 14 and 16 as illustrated in the figures, has the eyepiece inclined at an angle of 30° from the vertical which is considered to be a natural angle for viewing and for observing hand manipulation. The offset distance from the objective section to the eyepiece section and the distance from the objective section to the work area 30 places the hands in a natural position near the field when the viewer peers into the eyepiece, whether the viewer is standing or in a seated position.

Since the viewer is looking directly at the work area and the hands are naturally placed near the work area, the normal eye-hand coordination of the viewer is maintained.

The arrangement of the microscope 10 as illustrated also provides a large and clear unobstructed area between the microscope and the work area 30.

Figure 3:
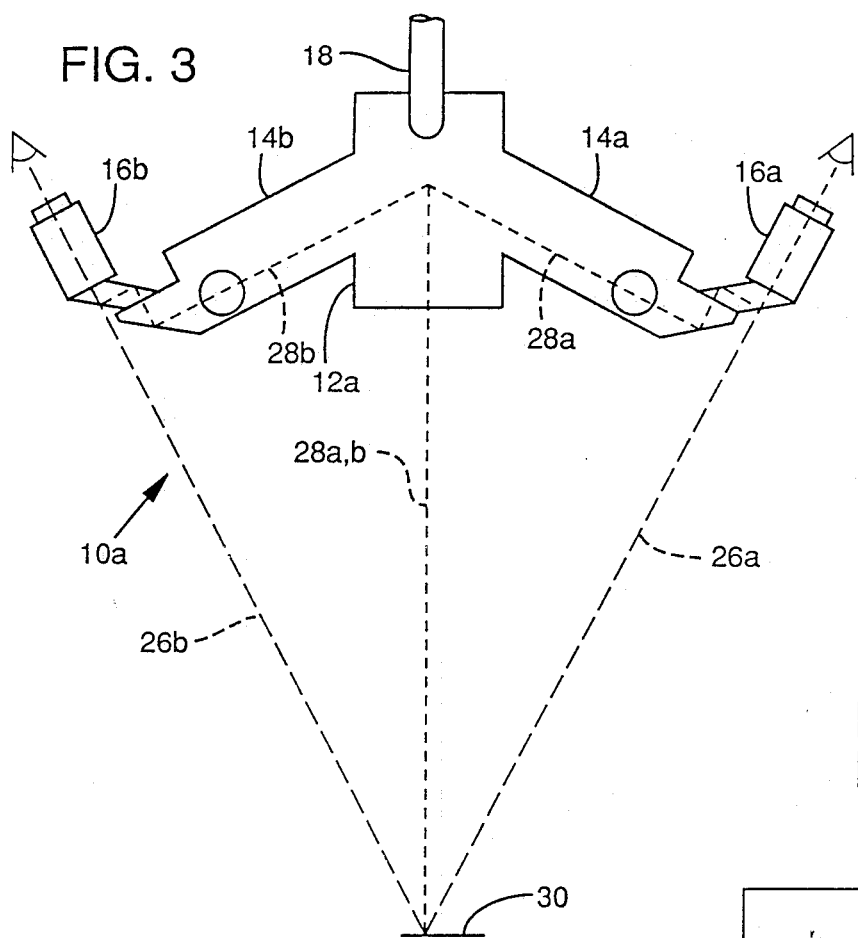
FIG. 3 is an alternate embodiment of the microscope.

An alternate embodiment of the microscope 10a is illustrated in FIG. 3. The microscope 10a has an additional zoom section 14b and an eyepiece section 16b positioned on the side of objective section 12a, opposite the zoom section 14a and eyepiece 16a. This provides two binocular viewing stations with each viewer having independent magnifications possible by zoom sections 14a and 14b. Additionally, the projected lines of sight 26a and 26b as viewed through the two groups of eyepieces 16a and 16b are aimed directly at the work area 30.

Other variations will be apparent upon examination of the description and drawings, and therefore the scope of invention is not to be limited to the embodiments set forth but is to be according to the appended claims.

What is claimed is:

1. A binocular microscope comprising;
   a housing having a plurality of sections, optical elements arranged in the plurality of sections, said elements magnifying an object in a work area, and the arrangement of said optical elements in said sections defining a folded optical axis;
   one of said sections being an eyepiece section for viewing an object in the work area through said optical elements, said eyepiece section having an optical axis which defines a projected line of sight through said eyepiece section, said projected line of sight intersecting said optical axis at the work area.

2. A binocular microscope as defined in claim 1 wherein said plurality of sections includes an objective section, a zoom section, and an eyepiece section, the objective section being vertically oriented and defining a vertical axis portion of the folded optical axis that is directed at the work area, the eyepiece section defining a projected line of sight directed at the work area and angled relative to said axis portion of the objective section, and a zoom section intermediate the objective section and the eyepiece section.

3. A binocular microscope as defined in claim 2 wherein the zoom section includes optical elements for varying the magnification of the microscope, and control means for manually controlling the arrangement of said optical elements for varying the magnification of the microscope.

4. A binocular microscope as defined in claim 3 including a light source for projecting light through the objective section and onto the work area.

5. A binocular microscope as defined in claim 4 including a second zoom section and a second eyepiece section inter-connected with said objective section, and further including a beam splitter for splitting the optical axis to provide a second path of the light from the objective section through the second zoom section and the second eyepiece section.

* * * * *